United States Patent
Hayes et al.

(10) Patent No.: US 9,809,525 B2
(45) Date of Patent: Nov. 7, 2017

(54) PRODUCTION OF TEREPHTHALIC ACID VIA REDUCTIVE COUPLING OF PROPIOLIC ACID OR PROPIOLIC ACID DERIVATIVES

(71) Applicant: The Procter & Gamble Company, Cincinnati, OH (US)

(72) Inventors: Jeffrey Charles Hayes, West Chester, OH (US); Hairong Guan, Cincinnati, OH (US); Dimitris Ioannis Collias, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/067,212

(22) Filed: Mar. 11, 2016

(65) Prior Publication Data

US 2016/0264506 A1  Sep. 15, 2016

Related U.S. Application Data

(60) Provisional application No. 62/132,550, filed on Mar. 13, 2015.

(51) Int. Cl.
| | |
|---|---|
| *C07C 51/15* | (2006.01) |
| *C07C 51/353* | (2006.01) |
| *C07C 51/377* | (2006.01) |
| *C07C 51/38* | (2006.01) |

(52) U.S. Cl.
CPC .............. *C07C 51/38* (2013.01); *C07C 51/15* (2013.01); *C07C 51/353* (2013.01); *C07C 51/377* (2013.01)

(58) Field of Classification Search
CPC ..... C07C 51/15; C07C 51/353; C07C 51/377; C07C 51/38
See application file for complete search history.

(56) References Cited

U.S. PATENT DOCUMENTS

| | | | |
|---|---|---|---|
| 2,729,674 A | 1/1956 | McKinnis et al. | |
| 2,864,854 A * | 12/1958 | McKinnis | C07C 51/38 556/125 |
| 4,317,659 A * | 3/1982 | Down | C01B 3/04 423/439 |
| 9,073,844 B2 | 7/2015 | Gossen et al. | |
| 2014/0012000 A1* | 1/2014 | Goossen | B01J 31/183 546/10 |

FOREIGN PATENT DOCUMENTS

WO   WO 2012/022801 A1   2/2012

OTHER PUBLICATIONS

Agenet et al., "Cotrimerizations of Acetyleneic Compounds," Organic Reactions, vol. 68, 2007, pp. 1-46 and 292-302.*
de Assis Filho et al., "Recovery of carbon dioxide from sugarcane fermentation broth in the ethanol industry," Food and Bioproducts Processing, 91 (2013) 287-291.*
Rodrigo, Sanjeewa et al. "Efficient and regioselective nickel-catalyzed [2+2+2] cyclotrimerization of ynoates and related alkynest" Organic & Biomolecular Chemistry, 2013, 11, 7653-7657.
Gooβen, Lukas J. et al., "Copper-Catalyzed Protodecarboxylation of Aromatic Carboxlyic Acids", Adv. Synth. Catal. 2007, 349, 2241-2246.
Obora, Yasushi et al., "NbCl₃-catalyzed [2+2+2] intermolecular cycloaddition of alkynes and alkenes to 1,3-cyclohexadiene derivatives", Org. Biomol. Chem., 2009, 7, 428-431.
Hilt, Gerhard et al. "Cobalt-Catalyzed Intermolecular [2+2+2] Cycloaddition for the Synthesis of 1,3-Cyclohexadienes", J. Org. Chem. 2008, 73, 5187-5190.
Collias, Dimitris I. et al.: "Biobased Terephtalic Acid Technologies: A Literature Review", Industrial Biotechnology, vol. 10, No. 2, Apr. 1, 2014, pp. 91-105.
Wael, Baidossi et al., "Homogeneous and biphasic oligomerization of terminal alkynes by some water soluble rhodium catalysts", Journal of Molecular Catalysis, vol. 85, No. 2, Nov. 1, 1993, pp. 153-162.
International Search Report and Written Opinion for (PCT/US2016/021995) dated May 27, 2016.

* cited by examiner

*Primary Examiner* — Paul A Zucker
*Assistant Examiner* — Mark Luderer
(74) *Attorney, Agent, or Firm* — Brent M. Peebles

(57) ABSTRACT

A method of making terephthalic acid via reductive coupling of two molecules of propiolic acid or propiolic acid derivatives is presented. The reductive coupling can be catalyzed by compounds comprising metals, and propiolic acid or propiolic acid derivatives can be produced from acetylene and carbon dioxide. At least 4 of the 8 carbons in the terephthalic acid are non-fossil-derived.

14 Claims, No Drawings

PRODUCTION OF TEREPHTHALIC ACID VIA REDUCTIVE COUPLING OF PROPIOLIC ACID OR PROPIOLIC ACID DERIVATIVES

FIELD OF THE INVENTION

The present invention generally relates to methods for the production of terephthalic acid (TPA) via reductive coupling of two molecules of propiolic acid or propiolic acid derivatives, followed by: 1) a reaction with ethylene and then dehydrogenation; or 2) a reaction with another propiolic acid or propiolic acid derivative and then decarboxylation; or 3) a reaction with acetylene. The reductive coupling of two molecules of propiolic acid or propiolic acid derivatives can be catalyzed by compounds comprising metals. Propiolic acid or propiolic acid derivatives can be produced from acetylene and carbon dioxide. At least 4 of the 8 carbons in the TPA of the present invention can be non-fossil-derived.

BACKGROUND OF THE INVENTION

TPA is currently produced via a catalytic and aerobic oxidation of para-xylene (pX), which in turn is produced from fossil resources. TPA is used primarily as a co-monomer in a condensation with mono ethylene glycol to produce poly(ethylene terephthalate) (PET) for plastic bottles, fibers, films, etc. Condensations of TPA with other glycols produce other various polyesters.

Currently, there is strong interest to improve the environmental profile of TPA, either by improving the environmental aspects of the pX oxidation process and/or producing TPA from non-fossil resources (i.e., renewable and inorganic resources; non-fossil-derived TPA), such as carbohydrates, lignin, inorganic salts, etc. More on the current process to produce fossil-derived TPA and pathways to produce non-fossil-derived TPA can be found in Collias et al. (2014) *Ind. Biotechnology* 10(2): 91-105.

Fossil-derived TPA contributes to greenhouse emissions due to its high fossil-derived carbon content. Furthermore, fossil resources, such as crude oil, natural gas, coal, peat, etc., are considered non-renewable materials, since they take hundreds of thousands of years to form naturally and are consumed quickly. On the other hand, renewable resources refer to materials that are produced via a natural process at a rate comparable to their rate of consumption (e.g., within a 100-year time frame). Renewable resources can be replenished naturally or via agricultural techniques. Examples of renewable resources include plants, such as sugar cane, sugar beets, corn, potatoes, citrus fruit, woody plants, lignocellulose, carbohydrate, hemicellulose, cellulosic waste, animals, fish, bacteria, fungi, and forestry products. Inorganic resources refer to inorganic salts, such as calcium carbonate, etc. As fossil resources become increasingly scarce and more expensive, exhibit higher price volatility, and become subject to regulations for fossil $CO_2$ emissions, there exists a growing need for non-fossil-derived TPA, which can serve as an alternative to fossil-derived TPA. Additionally, as natural gas in the U.S. displaces naphtha as a feedstock for the petrochemical industry, shortages of fossil-derived aromatic materials are expected in the future, and thus there will be an increasing need for non-fossil-derived aromatics.

Many attempts have been made over the last decades to make non-fossil-derived TPA (see Collias et al.). However, no process has yet demonstrated its commercial viability, i.e., high yield of and selectivity for non-fossil-derived TPA, low selectivity for side products, and mild process conditions. Accordingly, there is a need for methods for the production of non-fossil-derived TPA with commercial viability.

SUMMARY OF THE INVENTION

A method of making TPA is provided. In one embodiment of the present invention, the method includes reductive coupling of two molecules of propiolic acid or propiolic acid derivatives followed by reaction with ethylene and dehydrogenation. In another embodiment of the present invention, the method includes reductive coupling of two molecules of propiolic acid or propiolic acid derivatives followed by reaction with propiolic acid and decarboxylation. In yet another embodiment of the present invention, the method includes reductive coupling of two molecules of propiolic acid or propiolic acid derivatives followed by reaction with acetylene. Additional features of the invention may become apparent to those skilled in the art from a review of the following detailed description, taken in conjunction with the examples

DETAILED DESCRIPTION OF THE INVENTION

I. Definitions

As used herein, the term "fossil-derived" material refers to a material that is produced from fossil resources, such as crude oil, natural gas, coal, peat, etc.

As used herein, the term "non-fossil-derived" material refers to a material that is produced from non-fossil resources, i.e., renewable and inorganic resources.

As used herein, the term "renewable" material refers to a material that is produced from a renewable resource, which is a resource produced via a natural process at a rate comparable to its rate of consumption (e.g., within a 100 year time frame). The renewable resource can be replenished naturally, or via agricultural techniques. Non-limiting examples of renewable resources include plants (e.g., sugar cane, beets, corn, potatoes, citrus fruit, woody plants, lignocellulose, hemicellulose, and cellulosic waste), animals, fish, bacteria, fungi, and forestry products. These resources can be naturally occurring, hybrids, or genetically engineered organisms. Fossil resources, such as crude oil, natural gas, coal, and peat, which take longer than 100 years to form, are not considered renewable resources. In some embodiments, since at least part of TPA is derived from a renewable resource, which can sequester carbon dioxide, use of TPA can reduce global warming potential and fossil fuel consumption.

As used herein, the term "renewable content" refers to the amount of carbon from a renewable resource in a material as a percent of the weight (mass) of the total organic carbon in the material, as determined by ASTM D6866-10 Method B.

As used herein, the term "inorganic" material refers to a material that is produced from an inorganic resource, i.e., inorganic salt compound, such as calcium carbonate, etc.

II. Methods for the Production of TPA

Although not wishing to be bound by any theory, applicants believe that TPA can be produced via a metal-catalyzed regioselective, reductive coupling of two molecules of propiolic acid or propiolic acid derivatives to form a metallacycle. This metallacycle can then be reacted with either ethylene (reaction path in Scheme 1), or another propiolic acid compound (top reaction path in Scheme 2) to form an intermediate. This intermediate can form TPA via dehydrogenation when ethylene was used to react with the metallacycle, or via decarboxylation when propiolic acid or propiolic acid derivative was used to react with the metallacycle. Alternatively, reaction of the metallacycle with acetylene (bottom reaction path in Scheme 2) can form TPA directly.

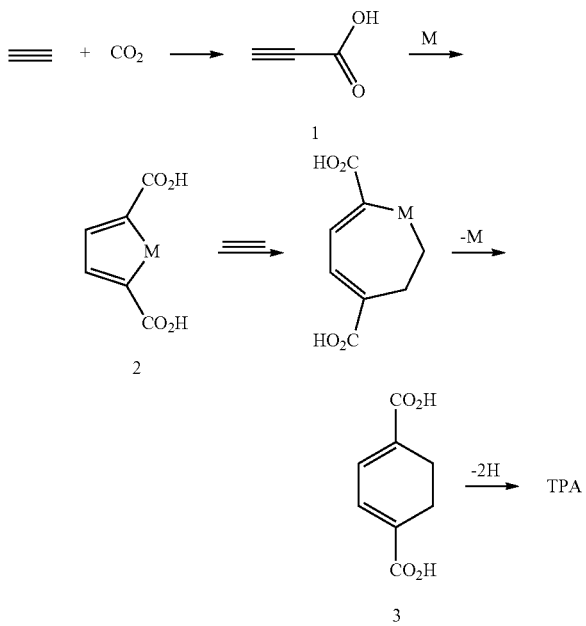

Scheme 1. TPA from Acetylene, CO₂, and Ethylene

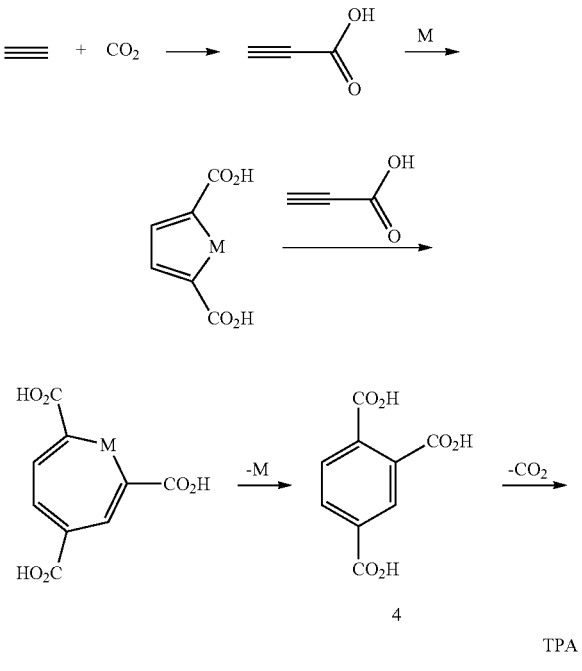

Scheme 2. TPA from Acetylene and CO₂

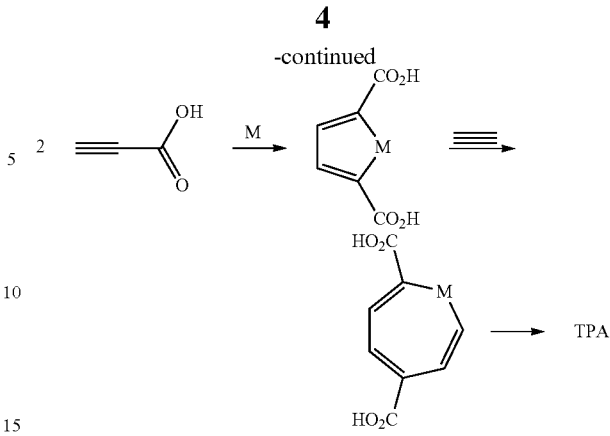

Propiolic acid or propiolic acid derivatives can be produced from the reaction of acetylene and carbon dioxide. Also, propiolic acid or propiolic acid derivatives can be formed from any other reaction path as known to those skilled in the art. Propiolic acid derivatives can be metal or ammonium salts of propiolic acid, alkyl esters of propiolic acid, amides of propiolic acid, or mixtures thereof. Non-limiting examples of metal salts of propiolic acid are sodium propiolate, potassium propiolate, calcium propiolate, or mixtures thereof. Non-limiting examples of alkyl esters of propiolic acid are methyl propiolate, ethyl propiolate, butyl propiolate, 2-ethylhexyl propiolate, or mixtures thereof.

For the purposes of the present invention, acetylene can be non-fossil-derived or fossil-derived. For example, non-fossil-derived acetylene can be prepared from bio-methane (i.e., methane derived from biomass) and fossil-derived acetylene can be prepared from natural gas or calcium carbide (produced from lime and coke at high temperature).

For the purposes of the present invention, carbon dioxide can be non-fossil-derived or fossil-derived. For example, non-fossil-derived carbon dioxide is a side product in: sugar fermentation to ethanol, non-fossil-derived ethylene oxidation to ethylene oxide, or steam reforming of non-fossil-derived methane. For example, fossil-derived carbon dioxide can be prepared during the steam reforming of natural gas or via carbon dioxide capturing and sequestration technologies (CCS) from steel mills (at least the part of carbon dioxide that is attributed to the coke oxidation, as the other part that is attributed to the limestone is considered non-fossil-derived for the purposes of this invention).

In one embodiment of the present invention, a method of making TPA includes reductive coupling of two molecules of propiolic acid or propiolic acid derivatives followed by reaction with ethylene and dehydrogenation. In another embodiment of the present invention, a method of making TPA includes reductive coupling of two molecules of propiolic acid or propiolic acid derivatives followed by reaction with propiolic acid or propiolic acid derivatives, and decarboxylation. In yet another embodiment of the present invention, a method of making TPA includes reductive coupling of two molecules of propiolic acid or propiolic acid derivatives followed by reaction with acetylene.

In one embodiment of the present invention, the reductive coupling of two molecules of propiolic acid or propiolic acid derivatives includes a catalyst. In another embodiment of the present invention, the catalyst comprises a metal. Non-limiting examples of catalysts comprising a metal are catalysts with low-valent metals, such as $CoBr_2$(phosphine)/Zn/$ZnI_2$, Ni(COD)$_2$/phosphine (or carbene) (COD=1,5-cyclooctadiene), Mo(CO)$_6$/phosphine, and [Cp^RuCl$_2$]$_2$ (Cp^=cyclopentadienyl derivative). Non-limiting examples of metals are nickel, iron, cobalt, copper, palladium, and mixtures thereof.

In one embodiment of the present invention, the catalyst is homogeneous. In another embodiment of the present invention, the catalyst is heterogeneous. In one embodiment of the present invention, the method of making TPA is conducted in gas phase. In another embodiment of the present invention, the method of making TPA is conducted in liquid phase. In one embodiment of the present invention, the method of making TPA is conducted in a batch mode. In another embodiment of the present invention, the method of making TPA is conducted in a continuous mode. In yet another embodiment of the present invention, the method of making TPA is conducted in a semi-continuous mode.

In one embodiment of the present invention, the method of making TPA is conducted in a flow reactor. Non-limiting examples of flow reactors are plug flow reactors, trickle bed reactors, fluidized bed reactors, and membrane reactors. In another embodiment of the present invention, the method of making TPA is conducted in a continuous stirred-tank reactor (CSTR).

In one embodiment of the present invention, the method of making TPA is conducted in a single stage mode. In another embodiment of the present invention, the method of making TPA is conducted in a multi-stage mode.

In one embodiment of the present invention, at least 4 of the 8 carbons in the TPA are non-fossil derived. In another embodiment of the present invention, at least 6 of the 8 carbons in the TPA are non-fossil derived. In yet another embodiment of the present invention, all carbons in the TPA are non-fossil derived.

In one embodiment of the present invention, at least 4 of the 8 carbons in the TPA are renewable. In another embodiment of the present invention, at least 6 of the 8 carbons in the TPA are renewable. In yet another embodiment of the present invention, all carbons in the TPA are renewable.

In one embodiment of the present invention, the method to produce TPA has a selectivity for TPA of at least about 50 mol %. In another embodiment of the present invention, the method to produce TPA has a selectivity for TPA of at least about 80 mol %. In yet another embodiment of the present invention, the method to produce TPA has a selectivity for TPA of at least about 90 mol %.

In one embodiment of the present invention, the method to produce TPA has a conversion of propiolic acid or propiolic acid derivatives of at least about 50 mol %. In another embodiment of the present invention, the method to produce TPA has a conversion of propiolic acid or propiolic acid derivatives of at least about 80 mol %. In yet another embodiment of the present invention, the method to produce TPA has a conversion of propiolic acid or propiolic acid derivatives of at least about 90 mol %.

III Test and Calculation Procedure

The renewable content of a material is measured using the ASTM D6866 method, which allows the determination of the renewable content of materials using radiocarbon analysis by accelerator mass spectrometry, liquid scintillation counting, and isotope mass spectrometry. When nitrogen in the atmosphere is struck by an ultraviolet light produced neutron, it loses a proton and forms carbon that has a molecular weight of 14, which is radioactive. This $^{14}C$ is immediately oxidized into carbon dioxide, which represents a small, but measurable fraction of atmospheric carbon. Atmospheric carbon dioxide is cycled by green plants to make organic molecules during the process known as photosynthesis. The cycle is completed when the green plants or other forms of life metabolize the organic molecules producing carbon dioxide, which causes the release of carbon dioxide back to the atmosphere. Virtually all forms of life on Earth depend on this green plant production of organic molecules to produce the chemical energy that facilitates growth and reproduction. Therefore, the $^{14}C$ that exists in the atmosphere becomes part of all life forms and their biological products. These renewably based organic molecules that biodegrade to carbon dioxide do not contribute to global warming because no net increase of carbon is emitted to the atmosphere. In contrast, fossil fuel-based carbon does not have the signature radiocarbon ratio of atmospheric carbon dioxide. See WO 2009/155086, incorporated herein by reference.

The application of ASTM D6866 to derive a "renewable content" is built on the same concepts as radiocarbon dating, but without use of the age equations. The analysis is performed by deriving a ratio of the amount of radiocarbon ($^{14}C$) in an unknown sample to that of a modern reference standard. The ratio is reported as a percentage with the units "pMC" (percent modern carbon). If the material being analyzed is a mixture of present day radiocarbon and fossil carbon (containing no radiocarbon), then the pMC value obtained correlates directly to the amount of biomass material present in the sample. The modern reference standard used in radiocarbon dating is a NIST (National Institute of Standards and Technology) standard with a known radiocarbon content equivalent approximately to the year AD 1950. The year AD 1950 was chosen because it represented a time prior to thermo-nuclear weapons testing, which introduced large amounts of excess radiocarbon into the atmosphere with each explosion (termed "bomb carbon"). The AD 1950 reference represents 100 pMC. "Bomb carbon" in the atmosphere reached almost twice normal levels in 1963 at the peak of testing and prior to the treaty halting the testing. Its distribution within the atmosphere has been approximated since its appearance, showing values that are greater than 100 pMC for plants and animals living since AD 1950. The distribution of bomb carbon has gradually decreased over time, with today's value being near 107.5 pMC. As a result, a fresh biomass material, such as corn, could result in a radiocarbon signature near 107.5 pMC.

Fossil-derived carbon does not have the signature radiocarbon ratio of atmospheric carbon dioxide. Research has noted that fossil fuels and petrochemicals have less than about 1 pMC, and typically less than about 0.1 pMC, for example, less than about 0.03 pMC. However, compounds derived entirely from renewable resources have at least about 95 percent modern carbon (pMC), they may have at least about 99 pMC, including about 100 pMC.

Combining fossil carbon with present day carbon into a material will result in a dilution of the present day pMC content. By presuming that 107.5 pMC represents present day biomass materials and 0 pMC represents petroleum derivatives, the measured pMC value for that material will reflect the proportions of the two component types. A material derived 100% from present day soybeans would give a radiocarbon signature near 107.5 pMC. If that material was diluted with 50% petroleum derivatives, it would give a radiocarbon signature near 54 pMC.

A renewable content result is derived by assigning 100% equal to 107.5 pMC and 0% equal to 0 pMC. In this regard, a sample measuring 99 pMC will give an equivalent renewable content result of 93%.

Assessment of the materials described herein was done in accordance with ASTM D6866, particularly with Method B. The mean values encompass an absolute range of 6% (plus and minus 3% on either side of the renewable content value) to account for variations in end-component radiocarbon signatures. It is presumed that all materials are present day or fossil in origin and that the desired result is the amount of bio-component "present" in the material, not the amount of bio-material "used" in the manufacturing process.

Other techniques for assessing the renewable content of materials are described in U.S. Pat. Nos. 3,885,155, 4,427,884, 4,973,841, 5,438,194, and 5,661,299, and WO 2009/155086, each incorporated herein by reference.

For example, TPA contains eight carbon atoms in its structural unit. If TPA is derived from a renewable resource, then it theoretically has a renewable content of 100%, because all of the carbon atoms are derived from a renewable resource.

VI EXAMPLES

The following examples are provided to illustrate the invention, but are not intended to limit the scope thereof.

Example 1—Synthesis of Ethyl Propiolate

Propiolic acid (310 µL, 5 mmol; Alfa Aesar, Ward Hill, Mass.; catalog # A13245) was dissolved in 13 mL of ethanol, giving a colorless solution, to which concentrated sulfuric acid (139 µL, 2.5 mmol) was added. The resulting mixture was heated to reflux for 24 h, and then treated with 13 mL of water before being extracted with dichloromethane (10 mL; three times). The combined organic layers were washed with water (10 mL; three times) and brine (10 mL), and then dried over anhydrous $Na_2SO_4$ (Thermo Fisher Scientific, Pittsburgh, Pa.; catalog # S421-3). Removal of the solvent under vacuum afforded the product as a light yellow color oil (177 mg, 36% yield). $^1$H NMR (400 MHz, $CDCl_3$, δ): 4.26 (q, $^3J_{H-H}$=7.1 Hz, $CH_2$, 2H), 2.92 (s, C≡CH, 1H), 1.33 (t, $^3J_{H-H}$=7.2 Hz, $CH_3$, 3H).

Example 2—Catalytic [2+2+2] Cyclotrimerization of Ethyl Propiolate

Under an argon atmosphere, $Ni(COD)_2$ (5.5 mg, 0.020 mmol; Acros, Pittsburgh, Pa.; catalog #223970050) and $PPh_3$ (15.6 mg, 0.060 mmol; Sigma-Aldrich Co., St. Louis, Mo.; catalog # T84409) were mixed in 10 mL of toluene at 23° C. The resulting mixture was stirred at this temperature for 5 min to produce a stock solution of the catalyst. A portion of the stock solution (375 µL) was added to a 10 mL scintillation vial under an argon atmosphere and the volume was brought to 2 mL with toluene, followed by the addition of ethyl propiolate (152 µL, 1.5 mmol). The reaction was complete within 2 h, producing a mixture of 1,2,4- and 1,3,5-isomers in a 97:3 molar ratio. The 1,2,4-isomer (triethyl trimellitate) was separated from the isomeric mixture using column chromatography (eluted with diethyl ether/hexanes) and isolated in 92% yield. $^1$H NMR (400 MHz, $CDCl_3$, δ): 8.41 (1H, d, $^4J_{H-H}$=1.7 Hz, ArH), 8.20 (1H, dd, $^3J_{H-H}$=7.9 Hz, $^4J_{H-H}$=1.7 Hz, ArH), 7.76 (1H, d, $^3J_{H-H}$=7.9 Hz, ArH), 4.50-4.35 (6H, m, $CH_2$), 1.50-1.35 (9H, m, $CH_3$); $^{13}C\{^1H\}$ NMR (101 MHz, $CDCl_3$, δ): 167.24, 166.70, 165.07, 136.36, 132.77, 132.17, 132.10, 130.19, 128.95, 62.09, 62.03, 61.78, 14.36, 14.20, 14.15.

Example 3—Hydrolysis of the 1,2,4- and 1,3,5-isomers of Benzenetricarboxylic Acid Triethyl Ester to Trimellitic Acid and Trimesic Acid The 97:3 mixture of 1,2,4- and 1,3,5-isomers of benzenetricarboxylic acid triethyl ester (294 mg, 1.0 mmol) was dissolved in 40 mL of water-ethanol (1:1) mixture. NaOH (240 mg, 6.0 mmol) was added, and the resulting mixture was stirred at 23° C. for 12 h. Upon completion of the reaction, the solution was acidified using a concentrated HCl solution (the acidity of the solution was monitored using pH paper). The resulting solution was concentrated under vacuum, and the residue was extracted with diethyl ether (15 mL; three times). The combined organic layers were dried over anhydrous $Na_2SO_4$ and then pumped to dryness. A mixture of 1,2,4- and 1,3,5-isomers of benzenetricarboxylic acid (94:6 molar ratio) was isolated in 77% combined yield (161 mg, light yellow solid). $^1$H NMR (400 MHz, DMSO-$d_6$, δ): 1,2,4-isomer: 13.44 (br, COOH, 3H), 8.21 (d, $^4J_{H-H}$=1.2 Hz, ArH, 1H), 8.12 (dd, $^3J_{H-H}$=8.0 Hz, $^4J_{H-H}$=1.6 Hz, ArH, 1H), 7.74 (d, $^3J_{H-H}$=8.0 Hz, ArH, 1H); 1,3,5-isomer: 13.44 (br, COOH, 3H), 8.64 (s, ArH, 3H).

Example 4—Synthesis of Sodium Propiolate and Catalytic [2+2+2] Cyclotrimerization of Sodium Propiolate to Trimellitic Acid and Trimesic Acid In a 10 mL scintillation vial under an argon atmosphere, NaH (48 mg, 2.0 mmol; Sigma-Aldrich Co., St. Louis, Mo.; catalog #452912) was dissolved in 3 mL of dry THF, followed by the addition of propiolic acid (124 µL, 2.0 mmol; Alfa Aesar, Ward Hill, Mass.; catalog # A13245). The resulting mixture was stirred at 23° C. in the dark for 1 h, producing sodium propiolate as a white suspension. In a separate 10 mL scintillation vial under an argon atmosphere, $Ni(COD)_2$ (11 mg, 0.040 mmol; Acros, Pittsburgh, Pa.; catalog #223970050) and $PMe_3$ (12.4 µL, 0.12 mmol; Sigma-Aldrich Co., St. Louis, Mo.; catalog #323322) were dissolved in 2 mL of dry THF and stirred at 23° C. for 5 min. The suspension of sodium propiolate in THF was added, and the reaction mixture was stirred at 23° C. in the dark for 1 h. Upon completion of the reaction, the resulting suspension was gravity filtered. Both filtrate and precipitate were acidified using a dilute HCl solution (the acidity was monitored using pH paper). Products in both acidified filtrate and precipitate were extracted into diethyl ether separately. Organic layers were dried by passing through a small column packed with anhydrous $Na_2SO_4$ (Thermo Fisher Scientific, Pittsburgh, Pa.; catalog # S421-3), after which the solvent was removed under vacuum. Crude products were characterized by 1H NMR spectroscopy. Products were present only in the precipitate and 1,2,4-isomer and 1,3,5-isomer molar ratio was determined to be 6:1.

Example 5—Decarboxylation of Trimellitic Acid and Trimesic Acid

A 94:6 mixture of trimellitic acid and trimesic acid (50 mg, 0.24 mmol) and $Cu_2O$ (41 mg, 0.29 mmol; Sigma-Aldrich Co., St. Louis, Mo.; catalog #208825) were treated with 5 mL of water and heated to reflux at 180° C. for 8 h. Upon completion of the reaction, the resulting mixture was gravity filtered, and the filtrate was extracted with diethyl ether (10 mL; three times). The combined organic layers were dried over anhydrous $Na_2SO_4$ (Thermo Fisher Scientific, Pittsburgh, Pa.; catalog # S421-3) and the solvent was removed under vacuum. The resulting crude mixture was characterized by $^1$H NMR spectroscopy, which showed that the conversion to TPA was 83%. $^1$H NMR (400 MHz, DMSO-$d_6$, δ): 8.04 (s, ArH, 4H).

Every document cited herein, including any cross referenced or related patent or patent application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of the present invention.

What is claimed is:

1. A method of making terephthalic acid comprising reductive coupling of two molecules of propiolic acid or propiolic acid derivatives followed by reaction with ethylene and dehydrogenation, wherein said reductive coupling comprises a catalyst, and wherein said catalyst comprises a metal selected from the group consisting of zinc, molybdenum, ruthenium, nickel, iron, cobalt, copper, palladium, and mixtures thereof.

2. The method of claim 1, wherein said ethylene is non-fossil-derived.

3. The method of claim 1, wherein said propiolic acid or propiolic acid derivatives are produced by reaction of acetylene and carbon dioxide.

4. The method of claim 3, wherein said carbon dioxide is non-fossil-derived.

5. The method of claim 4, wherein said carbon dioxide is a by-product of an ethanol fermentation facility.

6. The method of claim 3, wherein said acetylene is non-fossil-derived.

7. The method of claim 1, wherein at least 4 of the 8 carbons in said terephthalic acid are non-fossil-derived.

8. A method of making terephthalic acid comprising reductive coupling of two molecules of propiolic acid or propiolic acid derivatives followed by reaction with acetylene, wherein said reductive coupling comprises a catalyst, and wherein said catalyst comprises a metal selected from the group consisting of zinc, molybdenum, ruthenium, nickel, iron, cobalt, copper, palladium, and mixtures thereof.

9. The method of claim 8, wherein said propiolic acid or propiolic acid derivatives are produced by reaction of acetylene and carbon dioxide.

10. The method of claim 9, wherein said carbon dioxide is non-fossil-derived.

11. The method of claim 10, wherein said carbon dioxide is a by-product of an ethanol fermentation facility.

12. The method of claim 8, wherein said acetylene is non-fossil-derived.

13. The method of claim 9, wherein said acetylene is non-fossil-derived.

14. The method of claim 8, wherein at least 4 of the 8 carbons in said terephthalic acid are non-fossil-derived.

* * * * *